United States Patent [19]

Alburn et al.

[11] 3,997,594
[45] * Dec. 14, 1976

[54] HYDROXAMIC ACIDS OF ALICYCLIC AMINO ACIDS

[75] Inventors: Harvey E. Alburn, West Chester; Donald E. Clark, Norristown; Norman H. Grant, Wynnewood; Milton Lapidus, Rosemont, all of Pa.

[73] Assignee: American Home Products Corporation, New York, N.Y.

[ * ] Notice: The portion of the term of this patent subsequent to Nov. 21, 1989, has been disclaimed.

[22] Filed: July 28, 1975

[21] Appl. No.: 599,615

Related U.S. Application Data

[63] Continuation-in-part of Ser. No. 464,372, April 26, 1974, abandoned, which is a continuation-in-part of Ser. No. 255,747, May 22, 1972, abandoned, which is a continuation-in-part of Ser. No. 874,381, Nov. 5, 1969, Pat. No. 3,703,543.

[52] U.S. Cl. .................. 260/500.5 H; 424/315; 424/316
[51] Int. Cl.² ............. C07C 119/00; C07C 103/30
[58] Field of Search ................... 260/500.5 H

[56] References Cited

UNITED STATES PATENTS

| | | | |
|---|---|---|---|
| 2,943,092 | 6/1960 | Smrt et al. | 260/500.5 H |
| 3,206,455 | 9/1965 | Alburn et al. | 260/239.1 |
| 3,703,543 | 11/1972 | Alburn et al. | 260/500.5 H |

Primary Examiner—Joseph E. Evans
Attorney, Agent, or Firm—Stephen Venetianer

[57] ABSTRACT

The compounds are hydroxamic acids of alicyclic amino acids, and esters of said compounds, all of which have valuable pharmacodynamic properties in that they suppress the immune response in warm-blooded animals.

2 Claims, No Drawings

HYDROXAMIC ACIDS OF ALICYCLIC AMINO ACIDS

This application is a continuation-in-part of application Ser. No. 464,372 filed Apr. 26, 1974 now abandoned which is a continuation-in-part application of Ser. No. 255,747 filed May 22, 1972 now abandoned which is a continuation-in-part of Ser. No. 874,381 filed Nov. 5, 1969 now U.S. Pat. No. 3,703,543.

DESCRIPTION OF THE INVENTION

This invention relates generally to novel chemical compounds having valuable pharmacodynamic properties and to processes for preparing said compounds.

The novel compounds of the invention are the hydroxamic acids and esters of 1-aminocyclopentanecarboxylic acid encompassed within the following general formula:

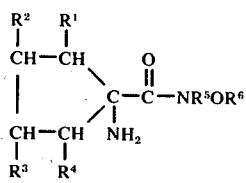
(I)

wherein each of $R^1$, $R^2$, $R^3$ and $R^4$ is selected from the group consisting of hydrogen, lower alkyl, lower alkoxy, hydroxy, halogen, nitro and amino, with the proviso that at least 2 of $R^1$, $R^2$, $R^3$ and $R^4$ are always hydrogen; and each of $R^5$ and $R^6$ is selected from the group consisting of hydrogen, lower alkyl, phenyl and phenyl (lower) alkyl: and the pharmaceutically accepted acid-addition salts thereof. The phenyl and phenyl(lower)alkyl groups may also be substituted in any one or two positions on the benzene ring by a substituent selected from the group consisting of lower alkyl, lower alkoxy, hydroxy, halogen, nitro and amino.

Preferred compounds are of the following formula:

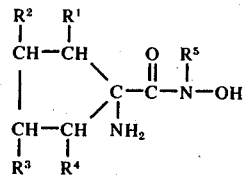

wherein:

$R^1$ and $R^4$ are selected from the group consisting of hydrogen, methyl, methoxy, hydroxy, nitro and amino; $R^2$ and $R^3$ are hydrogen, with the proviso that at least one of $R^1$ and $R^4$ is always hydrogen; $R^5$ is selected from the class consisting of hydrogen and lower alkyl; and the pharmaceutically-accepted acid-addition salts thereof.

Especially preferred compounds are of the following formula:

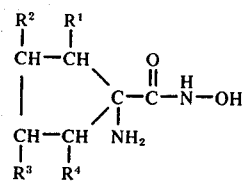

wherein:

$R^1$ and $R^4$ are selected from the class consisting of hydrogen, methyl and methoxy; $R^2$ and $R^3$ are hydrogen, with the proviso that at least one of $R^1$ and $R^4$ is always hydrogen; and the pharmaceutically-accepted acid-addition salts thereof.

The novel compounds of formula (I) above may conveniently be prepared by heat-reacting a selected hydroxylamine derivative with a selected 1-aminocyclopentanecarboxylic acid N-carboxyanhydride (NCA) in accordance with the following scheme:

(A)

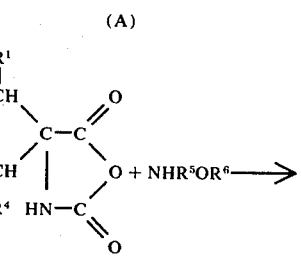

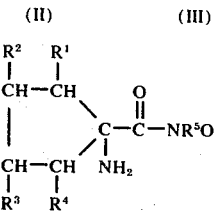

(I)

wherein $R^1$, $R^2$, $R^3$, $R^4$, $R^5$ and $R^6$ have the same meanings described hereinbefore.

The reactants (III), i.e. the hydroxylamine derivatives, employed in the preparative process illustrated by the above reaction scheme are known compounds which are readily available from commercial sources. The reactants (II), i.e. the NCA's of the 1-aminocycloalkylcarboxylic acids, which are not commercially available, can easily be prepared in accordance with standard organic procedures well known to those skilled in the art. For example, a procedure which has been employed to synthesize the anhydrides of formula (II) above is described in U.S. Pat. No. 3,206,455 "Process for Producing 6-(α-aminoacylamino) Penicillanic Acids", H. E. Alburn and N. H. Grant.

It has been discovered that compounds of formula (I) meeting the described qualifications have valuable pharmacological properties. More specifically, said compounds have been found to have unexpected anti-immune activity in warm-blooded animals as referred to in greater detail hereinafter.

The immune response, i.e., production of antibodies, is the means by which immunity to infectious disease is generated, and is an expression of the warm-blooded animal body's biochemical integrity. Malfunctions of this natural defense mechanism are known collectively as the immunopathies. These are characterized by altered response to external antigens, i.e., the manifestation of atopy or an allergy. They also include the auto-immune phenomena. The animal body is normally tolerant to its own tissues and does not treat them as antigens (foreign substances). A breakdown of this tolerance (natural homoestatic mechanisms) is the basis of those pathologic entities grouped under the term, auto-immune diseases. In addition to the immunopathies, normal functioning of the immune system can be disadvantageous, for example, by causing rejection of transplanted tissues or organs. Obviously, suppression of the immune response can be of major therapeutic importance in particular instances.

Suppression of the immune response was initially observed after X-ray and cortisone treatment, and can now be achieved by certain of the agents initially developed for use in cancer chemotherapy. In addition to the corticosteroids, these compounds can be divided into three major classifications; the alkylating agents (nitrogen mustards), purine antimetabolites (6-mercaptopurine) and the folic acid antagonists (methotrexate). Remarkable success in the treatment of non-neoplastic (autoimmune) diseases, and prolongation of homografts with these anti-neoplastic agents has stimulated research into this area of increasing interest and practical importance.

Unfortunately, of the heretofore known groups of compounds referred to above as having the desirable anti-immune activity, the alkylating agents are known to be carcinogenic and mutagenic, while the purine analogues are potentially so since they are incorporated into DNA. Further, the toxicity of the folic acid antagonists and corticosteroids are well known. Thus, from the method of treatment aspect of the present invention, such invention, in its broadest concept, also resides in the method of suppressing the immune response in a warm-blooded animal by administering to said animal, in which said response is undesirable, a therapeutically active amount of a compound selected from the group consisting of those having the general formula (I) as defined hereinbefore.

It has been well established that agents which are effective in suppressing the immune response are active also in preventing both the clinical and histopathologic changes which occur when test animals are challenged intravenously or orally with pretreated sheep red cells, as referred to in greater detail hereinafter. Such agents include the compounds of thioguanine, Imuran, 6-mercaptopurine, cyclophosphamide, methotrexate and cortisone, all of which have been shown to be active in warm-blooded animal immunopathies. Thus, the aforesaid challenge of test animals dosed with a specific compound may serve as a test standard for activity of other compounds with respect to the suppression of the immune response in general. (cf. H. C. Nathan et al. "Detection of Agents Which Interfere with the Immune Response"; Proc. Soc. Exp. Biol. & Med., 107, 796 (1961).

In accordance with the test described in the Nathan et al article identified above, preliminary preparations therefor are as follows: Male albino mice, having a body weight of 18–20 mgs. are selected as the test animals. The test standard compound is 6-mercaptopurine; and the vehicle for both the test standard compound and the compounds to be tested for the anti-immune activity, comprises a 0.5 percent solution of carboxymethyl cellulose (CMC) in distilled water (USP). The challenging material (i.e., the antigen) used in the test is prepared by (a) exposing sterile, washed sheep cells for 10 min. at 37° C. to an equal volume of 1:10,000 tannic acid in buffered saline solution, (b) collecting the treated cells by centrifugation; (c) washing the cells with similar buffered saline; (d) then resuspending the cells in the aforesaid 0.5 percent solution of CMC in distilled water. The buffered saline is preferably comprised of saline (0.85 percent NaCl mixed with an equal volume of buffer (29.9 ml. M/15 $KH_2PO_4$ + 76.0 ml. M/15 $Na_2HPO_4$).

In actual procedure of the Nathan et al test, the test animals are initially challenged intravenously with 0.25 ml. of a 30 percent buffered suspension of sheep red cells which have been pretreated as described hereinbefore. Treatment of the test animals with the selected test agent and the reference standard, 6-mercaptopurine, is initiated immediately after injection of the aforesaid antigen. Appropriate untreated antigen control animals are included. At selected intervals of time, the mice are bled from the heart, the serum separated and pooled for each treatment group and the hemogglutinin titer determined by serial 2-fold dilutions in test tubes as described by A. B. Stavitsky, J. Immunol. 72,360 (1964) and/or by the known microtiter method employing cup plate assemblies. The hemogglutinin is the host's antibody to the antigen, sheep red cells.

The activity of the compounds tested with respect to suppression of the immune response is determined as follows:

The score for each tube is multiplied by the appropriate exponent of the 2-fold dilution series, and the values summed for each series. The index of drug effect for the compound under test is obtained as a ratio of these sums for the treated to the untreated control, as set forth in the aforesaid Nathan et al article, wherein the antibody index (A.I.) is determined in accordance with the following formula:

$$A.I. = \frac{(S_1 + 2S_2 + 3S_3 + \ldots nSn)_T}{(S_1 + 2S_2 + 3S_3 + \ldots nSn)_C}$$

wherein
T = treated series
C = control series
$n$ = the exponent of dilution (tube number in the 2-fold series); and
S = the agglutination score.

It is also now well known that agents which are effective in suppressing the immune response are active also in preventing both the clinical and histopathologic changes which occur in experimental allergic encephalomyelitis (EAE). Such agents include the compounds thioguanine, Imuran, 6-mercaptopurine, cyclophosphamide, methodtrexate and cortisone, all of which have been shown to be active in suppressing the immune response. Thus, the disease EAE may serve as a test standard for the suppression of the immune processes in general. (cf. N. W. Brandriss, J. W. Smith, R. N. Friedman, "Suppression of Allergic Encephalomyelitis by Antimetabolites"; Ann. N.Y. Acad. Sci. 122:356, 1965.)

EAE is characterized by a delayed (cellular) hypersensitivity which is tissue specific and results in clinical paralysis of the animal. Histopathological lesions of the spinal cord and brain caused by said disease resemble those in demyelinating disease, and it is thus classified as an experimental autoallergic or auto-immune disease. (cf. B. H. Waksman, "Experimental Allergic Encephalomyelitis and the 'Auto-allergic' Diseases", I. Arch. Allerg. appl Immunol., 14 (Suppl)1, 1959; and I. R. Mackay and F. M. Burnet, "Auto-Immune Diseases, Pathogenesis, Chemistry and Therapy", Charles C. Thomas, Springfield, 1963.)

The surprising efficacy of the compounds of formula (I) above in both of the accepted tests described hereinbefore has clearly indicated that they are extremely active, relatively non-toxic, long-acting immuno-suppressive agents. Further, their long duration of action has indicated that only relatively low and infrequent dose schedules are required to obtain therapeutic effectiveness.

In the exercising of the method of the invention, the compounds of formula (I) used therein may be administered alone or in combination with pharmaceutically acceptable carriers, the proportion of which is determined by the solubility and chemical nature of the compound selected, the chosen route of administration, and standard pharmaceutical practice. For example, they may be administered orally in the form of tablets or capsules, which may contain conventional excipients, or in the form of solutions; or they may be injected parenterally, that is intramuscularly, intravenously or subcutaneously. For parenteral administration, they may be used in the form of sterile solutions containing other solutes, for example, enough saline or glucose to make the solutions isotonic.

The dosage of the present therapeutic agents will vary with the form of administration and the particular compound chosen. It will generally be found that when the composition is administered orally, larger quantities of the active agent will be required to produce the same effect as a smaller quantity given parenterally. In general, the compounds of this invention are most desirably administered at a concentration level that will generally afford effective results without causing any harmful or deleterious side effects.

The compounds (1) of the present invention, when tested in accordance with either of the two test procedures given in detail hereinbefore, are effective to suppress the immune response at dosages in the range of about 10 to about 80 mg/kg. of body weight of the animals tested.

The following examples are illustrative of the preparation of the novel compounds of the invention which are useful in the suppression of the immune response in warm-blooded animals:

EXAMPLE I

1-Aminocyclopentanecarbohydroxamic Acid Hydrochloride

A mixture of 7.2 g. of hydroxylamine hydrochloride, 15 ml. of triethylamine, and 100 ml. of methanol was stirred until the solutes dissolved. There was then added 8.1 g. of 1-aminocyclopentane carboxylic acid N-carboxyanhydride (NCA), followed, after the initial gas evolution ceased, by another 8.1 g. batch. After stirring the mixture at room temperature for 30 minutes, 250 ml. of isopropanol was added. The system was filtered, the filtrate was evaporated nearly to dryness, and the concentrate was extracted with 100 ml. of water and adjusted to pH 2.0 with HCl. The extract was evaporated to near dryness, taken up in a mixture of 200 ml. of isopropanol and 50 ml. of methanol, concentrated to 50 ml., and chilled. The crystalline precipitate, weighing 9.5 g., was recrystallized from methanolisopropanol, finally yielding 6 g.

Calcd. for $C_6H_{12}N_2O_2 \cdot HCl$: C, 39.9; H, 7.2; N, 15.5, Found: C, 39.6; H, 7.7; N, 15.8.

In the experimental allergic encephalomyelitis test described hereinbefore, 50 mg. of the product per kilogram of body weight of the animal tested gave complete protection against paralysis.

EXAMPLE II

1-Amino-N-benzyloxycyclopentanecarboxamide

Eight grams of O-benzylhydroxylamine hydrochloride were treated with an equivalent amount of sodium methoxide in 100 ml. of methanol, and the sodium chloride was removed. After removal of the methanol, the O-benzylhydroxylamine was dissolved in 200 ml. of tetrahydrofuran, and to it was added a solution of 7.75 g. of N-carboxy-1-aminoclopentane carboxylic acid anhydride in 100 ml. of tetrahydrofuran. The mixture was allowed to stand at 4° for 4 days and was then filtered. The filtrate was evaporated to dryness and the residue was dissolved in 150 ml. of hot ethanol. A crystalline product formed on cooling. It weighed 5.7 g. and melted at 94°–96°.

Calcd. for $C_{13}H_{18}N_2O_2$: C, 66.6; H, 7.7. Found: C, 66.6; H, 7.4.

The compound was an orally effective anti-immune agent when tested in accordance with the EAE test procedure described hereinbefore.

EXAMPLE III

Following the procedure of Example I, a series of hydroxylamine derivatives are separately reacted with the NCA of 1-aminocyclopentanecarboxylic acid (ACPCA) to obtain the hydroxamic acid derivatives of the latter in the form of their HCl acid-addition salts having anti-immune activity, as set forth in Table A below:

TABLE A

| Hydroxylamine Derivative | Substituted NCA of 1-ACPCA | Hydroxamic Acid Derivative of the Amino Acid |
| --- | --- | --- |
| hydroxylamine | 2-ethyl-1-aminocyclopentane carboxylic acid | 2-ethyl-1-aminocyclopentanecarbohydroxamic acid |
| hydroxylamine | 3-methoxy-1-aminocyclopentane carboxylic acid | 3-methoxy-1-aminocyclopentanecarbohydroxamic acid |
| O-ethylhydroxylamine | 3-hydroxy-1-aminocyclopentane carboxylic acid | 3-hydroxy-1-amino-N-ethoxycyclopentanecarboxamide |

TABLE A-continued

| Hydroxylamine Derivative | Substituted NCA of 1-ACPCA | Hydroxamic Acid Derivative of the Amino Acid |
|---|---|---|
| O-propylhydroxyl-amine | 2-chloro-1-aminocyclo-pentane carboxylic acid | 2-chloro-1-amino-N-propoxycyclopentane-carboxamide |
| O-methylhydroxyl-amine | 2-fluoro-1-aminocyclo-pentane carboxylic acid | 2-fluoro-1-amino-N-methoxycyclopentane-carboxamide |
| hydroxylamine | 2-propyl-3-ethoxy-1-aminocyclopentane carboxylic acid | 2-propyl-3-ethoxy-1-aminocyclopentane-carbohydroxamic acid |

EXAMPLE IV

Following, in this instance, the procedure of Example II, another series of hydroxylamine derivatives are separately reacted with the selected NCA's of 1-aminocyclopentane carboxylic acid to obtain the hydroxamic acid derivatives of the latter in the form of their bases which have anti-immune activity, as set forth in Table B below:

TABLE B

| Hydroxylamine Derivative | Substituted NCA of 1-ACPCA | Hydroxamic Acid Derivative of the Amino Acid |
|---|---|---|
| O-phenylhydroxyl-amine | 2-nitro-1-aminocyclo-pentane carboxylic acid | 2-nitro-1-amino-N-phenoxycyclopentane carboxamide |
| O-phenylhydroxyl-amine | 3-ethyl-1-aminocyclo-pentane carboxylic acid | 3-ethyl-1-amino-N-phenoxycyclopentane carboxamide |
| O-benzylhydroxyl-amine | 2,3-dichloro-1-amino-cyclopentane carboxylic acid | 2,3-dichloro-1-amino-N-benzyloxycyclo-pentane carboxamide |

EXAMPLE V

1-Amino-N-methylcyclopentane-carbohydroxamic Acid

To a solution of 5.54 g. of N-methylhydroxylamine hydrochloride in 218 ml. of absolute ethanol was added 32.5 ml. of 2 M sodium methoxide. After stirring for one hour, sodium chloride was removed by filtration, and 10 grams of N-carboxy-1-aminocyclopentane carboxylic acid anhydride was added. After stirring for 2.5 hours, the system was allowed to stand at room temperature overnight. The precipitate was removed, and the filtrate was evaporated to dryness on a rotary evaporator. The product, weighing 7.7 g., was washed with ether.

In the EAE test, referred to hereinbefore, the titled product, at 50 mg. per kilograms body weight, gave 45% protection against paralysis.

EXAMPLE VI

Following the procedure of Example V, a series of hydroxamic acid derivatives are separately reacted with a selected substituted NCA of 1-aminocyclopentane carboxylic acid to obtain the hydroxamic acid derivatives of the latter in the form of their bases which have anti-immune activity, as set forth in Table C below:

TABLE C

| Hydroxylamine Derivative | Substituted NCA of 1-ACPCA | Hydroxamic Acid Derivative of the Amino Acid |
|---|---|---|
| N-propyl-O-ethyl-hydroxylamine | 2-propyl-1-aminocyclo-pentane carboxylic acid | 2-propyl-1-amino-N-propyl-N-ethoxy-cyclopentane carbox-amide |
| N-benzylhydroxyl-amine | 3-propoxy-1-amino-cyclopentane carboxylic acid | 3-propoxy-1-amino-N-benzyl-cyclopentane carbohydroxamic acid |
| N-phenoxyhydroxyl-amine | 2-chloro-1-aminocyclo-pentane carboxylic acid | 2-chloro-1-amino-N-phenoxy-cyclopentane carbohydroxamic acid |
| N-methyl-O-propyl-hydroxylamine | 1-aminocyclopentane carboxylic acid | 1-amino-N-methyl-N-propoxy-cyclopentane carboxamide |

We claim:
1. A compound of the following formula:

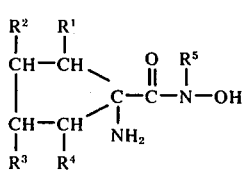

wherein:
R[1] and R[4] are selected from the group consisting of hydrogen, methyl, methoxy, hydroxy, nitro and amino; R[2] and R[3] are hydrogen, with the proviso that at least one of R[1] and R[4] is always hydrogen; R[5] is selected from the class consisting of hydrogen and lower alkyl; and the pharmaceutically-accepted acid-addition salts thereof.

2. A compound of the following formula:

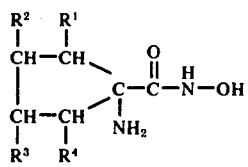

wherein:
R[1] and R[4] are selected from the class consisting of hydrogen, methyl and methoxy; R[2] and R[3] are hydrogen, with the proviso that at least one of R[1] and R[4] is always hydrogen; and the pharmaceutically-accepted acid-addition salts thereof.

* * * * *